(12) United States Patent
Montross

(10) Patent No.: US 11,589,900 B2
(45) Date of Patent: Feb. 28, 2023

(54) MODULAR FRAME

(71) Applicant: William Montross, Colorado Springs, CO (US)

(72) Inventor: William Montross, Colorado Springs, CO (US)

( * ) Notice: Subject to any disclaimer, the term of this patent is extended or adjusted under 35 U.S.C. 154(b) by 0 days.

(21) Appl. No.: 17/308,952

(22) Filed: May 5, 2021

(65) Prior Publication Data
US 2021/0346060 A1 Nov. 11, 2021

Related U.S. Application Data

(60) Provisional application No. 63/020,966, filed on May 6, 2020.

(51) Int. Cl.
*A61B 17/66* (2006.01)
*A61B 17/64* (2006.01)
*A61B 17/56* (2006.01)

(52) U.S. Cl.
CPC ............ *A61B 17/645* (2013.01); *A61B 17/66* (2013.01); *A61B 2017/564* (2013.01)

(58) Field of Classification Search
CPC .................... A61B 17/62; A61B 17/66; A61B 17/64–6491
See application file for complete search history.

(56) References Cited

U.S. PATENT DOCUMENTS

| | | | | |
|---|---|---|---|---|
| 5,540,686 A * | 7/1996 | Zippel | ................ | A61B 17/6441 606/56 |
| 2004/0073212 A1 * | 4/2004 | Kim | ....................... | A61B 17/62 606/56 |
| 2007/0049930 A1 * | 3/2007 | Hearn | .................... | A61B 17/66 606/56 |
| 2009/0177198 A1 * | 7/2009 | Theodoros | ............. | A61B 17/66 606/56 |
| 2010/0312243 A1 * | 12/2010 | Ross | .................... | A61B 17/645 606/56 |
| 2011/0245830 A1 * | 10/2011 | Zgonis | ...................... | A61F 5/05 606/57 |
| 2015/0216564 A1 * | 8/2015 | Salomone | .............. | A61B 17/62 606/56 |
| 2016/0066956 A1 * | 3/2016 | Siemer | ................... | A61B 17/62 606/56 |
| 2016/0278812 A1 * | 9/2016 | Riccione | ............ | A61B 17/6466 |
| 2017/0042580 A1 * | 2/2017 | Mannanal | ............ | A61B 17/645 |
| 2018/0317965 A1 * | 11/2018 | Robinson | ............... | A61B 17/62 |
| 2018/0368887 A1 * | 12/2018 | Lauf | ...................... | A61B 17/62 |
| 2020/0397481 A1 * | 12/2020 | Samchukov | ........... | A61B 17/62 |

* cited by examiner

*Primary Examiner* — Eduardo C Robert
*Assistant Examiner* — Michelle C Eckman
(74) *Attorney, Agent, or Firm* — BrainSpark Associates, LLC

(57) ABSTRACT

Disclosed are improved devices, systems and methods for external fixation and/or support of damaged or fractured limbs or other anatomies of a patient.

18 Claims, 22 Drawing Sheets

FIGURE 4B
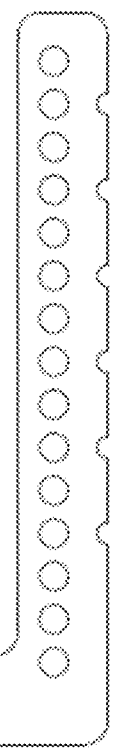
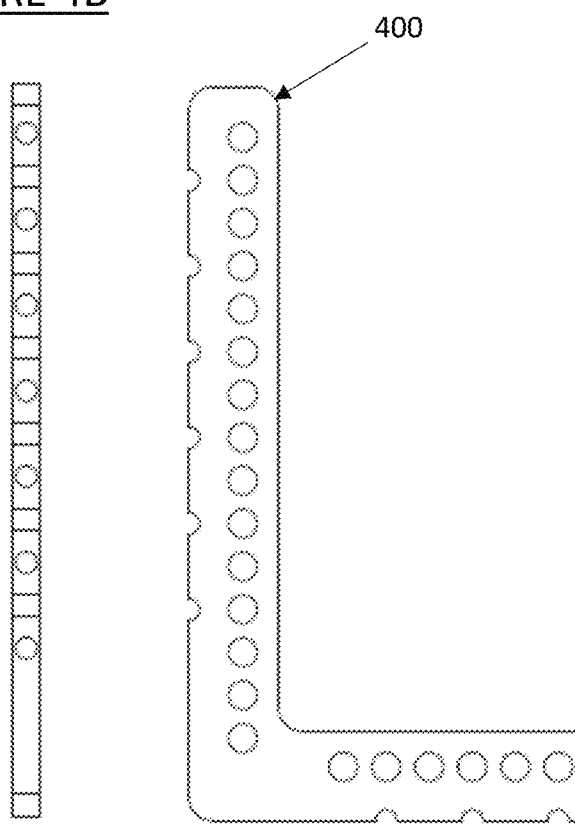
FIGURE 4A
FIGURE 4C

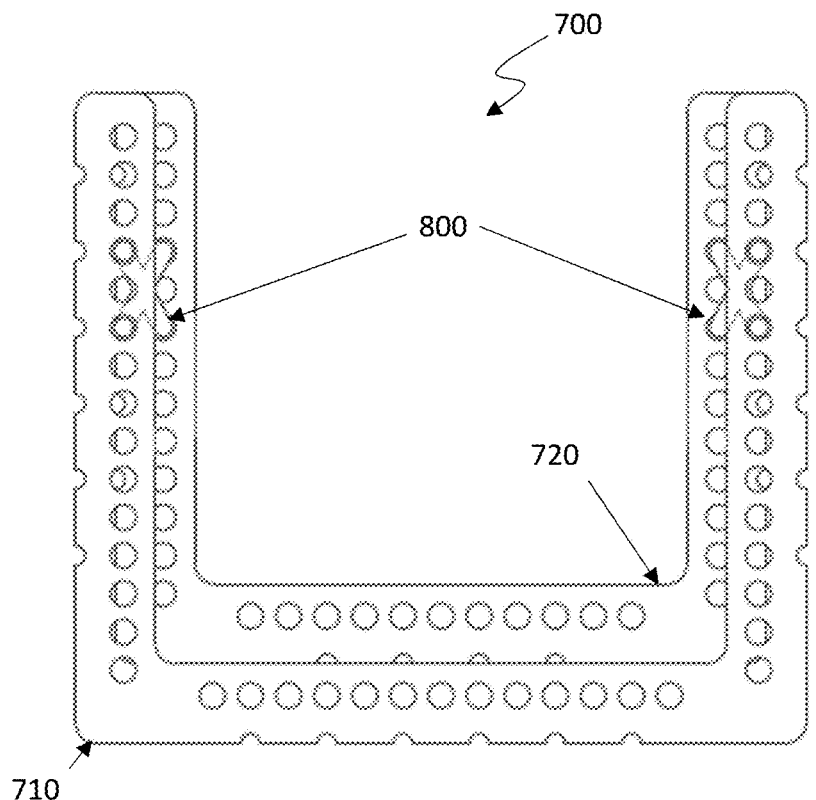
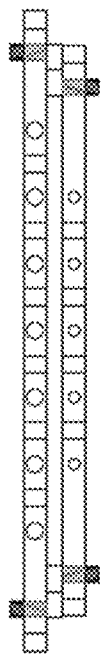
FIGURE 7A
FIGURE 7B
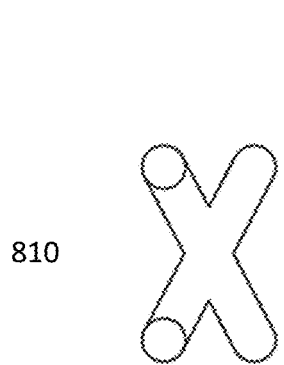
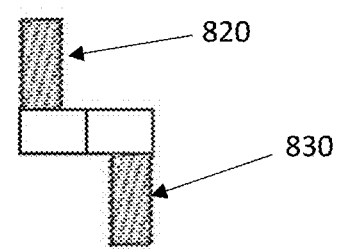
FIGURE 8A
FIGURE 8B

900

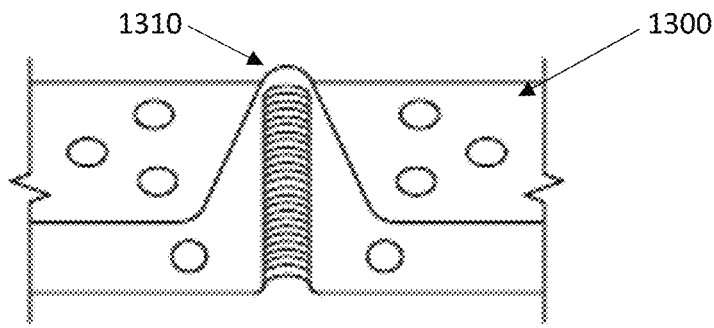
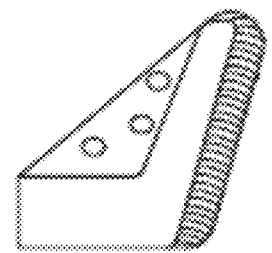
FIGURE 13A
FIGURE 13B
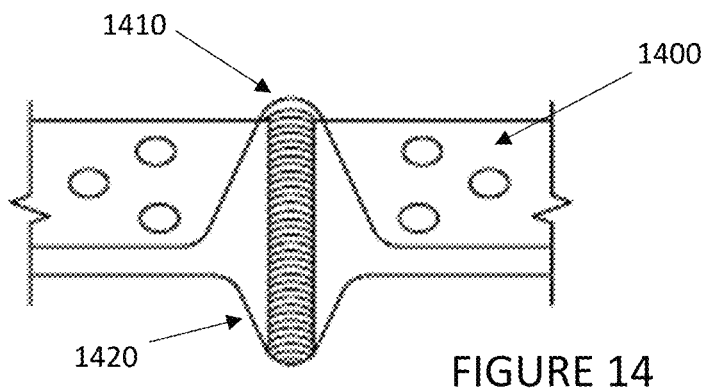
FIGURE 14
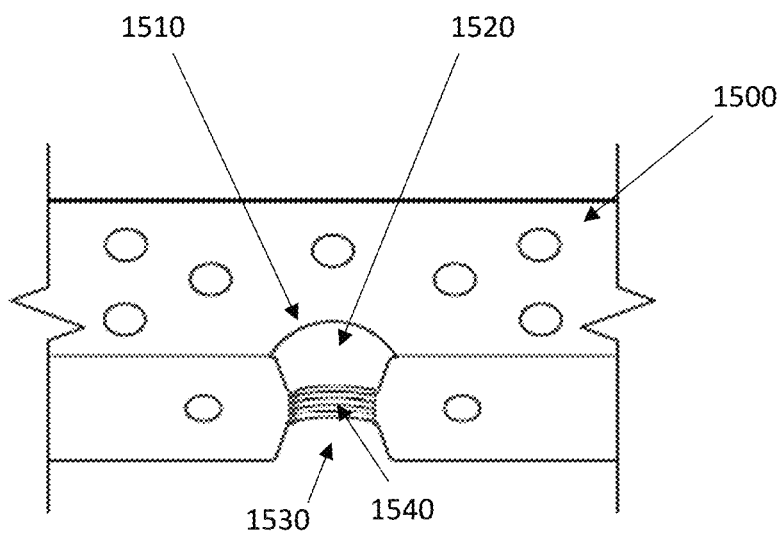
FIGURE 15

MODULAR FRAME

CROSS-REFERENCE TO RELATED APPLICATIONS

This application claims the benefit of U.S. Provisional Patent Application Ser. No. 63/020,966 entitled "Modular Frame," filed May 6, 2020. The disclosure of this document is incorporated by reference in its entirety.

TECHNICAL FIELD

The invention relates to improved devices, systems and methods for external fixation and/or support of damaged or fractured limbs or other anatomies of a patient. More specifically, embodiments disclosed herein can facilitate creation of a support and/or fixation frame that can be particularized for the needs of an individual patient, including the incorporation of various removeable and/or configurable components of the frame that allow the frame to be reconfigured in a variety of ways without requiring removal from and/or loss of support to the patient.

BACKGROUND OF THE INVENTION

Reduction is a medical procedure to restore a fracture or dislocation to the correct alignment. When a bone fractures, the fragments lose their alignment in the form of displacement or angulation. For the fractured bone to heal without substantial deformity the bony fragments must be re-aligned to their normal anatomical position. Orthopedic surgeons attempt to recreate the normal anatomy of the fractured bone by reduction.

Fractured bone reduction or treatment can include use of fixation methods that can reinforce the fractured bone and keep it aligned during healing, including use of external devices or casts as well as internal devices such as rods, bone plates and/or fasteners. Under certain circumstances, a physician may decide that external fixation is the best treatment for a patient. Fixation with external devices and assemblies includes surgical techniques for setting bone fractures and/or for limb lengthening that was first used more than a century ago. Since that time, the technique has evolved from being used primarily as a last resort fixation method to becoming a main stream technique used to treat a myriad of bone and soft tissue pathologies.

In some cases, external fixation can be accomplished by placing pins or screws into the bone of a patient and securing the pins through the use of an external frame assembly positioned at least partially outside the body. During the treatment, the external frame can hold bone fragments at adjustable spacing and angles to create a desired overall bone length and angular disposition of the bone fragments. To connect the external fixation device to the bone, pins can be placed, for example, on either side of the break in the bone and pass through the skin and sometimes the muscles. Sometimes wires can also be used with the pins, or in place of pins, to secure the bone pieces. The pins and/or wires can hold the bone in place and anchor the fixator securely, while also avoiding damage to vital structures, allowing access to the area of injury, and meeting the mechanical demands of the patient and the injury. Treatment using external fixation can take about 6 weeks for a simple fracture, and up to one year or longer for a more complicated fracture.

As compared to other fixation methods, external fixation devices can provide numerous advantages. When compared with internal plates and intramedullary nails, for example, external fixators can cause less disruption of the soft tissues, osseous blood supply, and periosteum. Accordingly, external fixation devices can be useful for soft tissue management in the setting of acute trauma with skin contusions and open wounds, in chronic trauma where the extremity is covered in thin skin grafts and muscle flaps, and in patients with poor skin whose healing potential is compromised as in the case of rheumatoid disease, peripheral vascular disease, diabetes mellitus, and Charcot disease. In addition, the temporary nature of the pins and wires can provide bony stability in the setting of osteomyelitis where the presence of internal implants make eradication of infection more challenging. The ability to avoid putting fixation into the infected area is equally beneficial.

Unlike internal plates and intramedullary nails, external fixators also provide postoperative adjustability. This allows the extremity to be manipulated in the operating room to gain exposures to fracture fragments. In the situation of limb lengthening or deformity correction, gradual manipulation is possible with frame adjustment over time. As a result, external fixations have found use in pediatric fracture care where open physes preclude intramedullary nailing. Leg length discrepancy can also be reliably treated with circular and monolateral design fixators.

Many different designs and arrangements of fixation frames are known in the art, but the existing designs suffer from a number of disadvantages. For instance, many have been characterized by requiring a multiplicity of rods or bars interconnecting pin-holders in the frames. Such has resulted in increased weight and bulk, and the complexity of the frames has interfered with surgical management during placement of the frames and adjustment of the bone segments interconnected by the frames. Others have lacked full adjustment capability, making adjustment of the frame difficult when assembled on the patient. Additionally, complexity in prior known construction introduces difficulties in properly assembling the frame on the patient and in subsequently tightening the various adjustable parts therein, to produce the necessary rigidity required if the bone segments attached by the frame are to be properly held.

In general, existing external fixation devices and assemblies still remain limited in their application for treatment of bone fractures. For example, while the devices known in the prior art can help provide valuable treatment of fractures, particularly in the surgical setting, existing devices can be somewhat cumbersome and limited in versatility. In particular, room for improvement exists in providing a lightweight fixation frame that can be particularized for the needs of an individual patient, including the incorporation of various removeable and/or configurable components of the frame that allow the frame to be reconfigured in a variety of ways without requiring removal from the patient, and which performs similar or superior to existing fixation frames and/or that can be produced at a reasonable cost. Thus, there is continued interest in providing improved external fixation devices that are more versatile and can be used, for example, as more ambulatory or portable devices.

BRIEF SUMMARY OF THE INVENTION

The present invention includes the realization of a need for an improved lightweight external fixation frame assembly which obviates many of the difficulties characterizing prior known fixation frames. In various embodiments, the devices and systems disclosed herein can facilitate creation of a support and/or fixation frame that can be particularized for the needs of an individual patient, including the incorporation of various removeable and/or configurable components of the frame that allow the frame to be reconfigured in a variety of ways without significantly affecting the strength and/or stability of the frame or requiring removal from the patient. Whenever necessary and/or desired, reconfiguring of the frame can allow a surgeon, physician and/or other caregiver to access virtually any area of the patient's anatomy to inspect and/or treat wounds, other injuries and/or an intended surgical site, as well as to allow access to many anatomical surfaces and/or other areas of the patient for additional treatments up to and including surgical procedures on the supported anatomy.

The present invention relates to orthopedic fixation systems, assemblies, devices and related methods for reduction of a fractured bone of a patient.

Various embodiments disclosed herein include the use of a wide variety of shaped support structures, including arched, square and/or rectangular support plates or blocks, which can be interconnected using a variety of rods and support connectors. Desirably, the support blocks include connection features that allow connecting rods to be attached at one or more angles, including straight rod supports as well as angled and/or curved support rods. The disclosed systems can desirably facilitate the use of different sized and/or shaped support rods and/or support blocks on a single patient, which can be particularly useful for treating patients who are highly muscularized or are extremely obese or those with atypical anatomical features. In many embodiments, the systems disclosed herein can provide an extremely strong, durable and/or rugged construct which can be configured to easily accommodate virtually any patient and/or anatomical situation, and which can be reconfigured without requiring removal from and/or loss of support to the patient's anatomy.

Other important features of the various designs disclosed herein facilitate the quick and convenient assembly, disassembly and/or repositioning of various frame components, which can facilitate faster access to various underlying anatomical regions to allow dressing changes and/or alteration of frame components, including an ability to change "levels" in an office and/or outpatient visit.

In various embodiments. the frame configuration can be particularly quick and easy to assemble and/or disassemble in a much more rapid fashion that with existing fixation frame designs.

In some embodiments, fixation rods and/or other components may optionally be attached outside of the post attachment holes, which reduces a need for such attachment mechanisms within the frame itself—thereby significantly reducing wasted space on the frame.

In at least one exemplary embodiment, a "squared-box" frame design can be utilized to provide additional open space between the patient's anatomy and frame components in a variety of locations as compared to a traditional rounded design, and the disclosed frame designs can also provide a significant increase in the number and/or distribution of "pin positions" and/or other connection points and/or locations for various frame components.

In various embodiments, frame components can utilized to quickly and easily "upsize" and/or "downsize" some portions and/or all of the frame at various anatomical locations on the patient. For example, an athletic and/or obese individual may have various enlarged anatomical features such as enlarged calves and/or thighs, with more normally sized and/or shaped feet and ankles. For these individuals, it may be desirous to assemble a modular frame having enlarged components in the calf or thigh region, while retaining more normally sized and/or shaped components in the foot and/or ankle region. In addition, the various disclosed embodiments can optionally include components can be shifted, rotated and/or tilted relative to other components in the frame, allowing a modular frame design to be constructed that accommodates enlarged and/or unusually shaped anatomy in various regions, as well as anatomy that may be disposed in a significantly lateral direction relative to the longitudinal axis of the frame.

The various modular frame components disclosed herein allow for removal and/or reconfiguration of individual frame components, most desirably without requiring removal and/or reconfiguration of other adjacent components. Unlike existing frame systems, that typically incorporate multiple nuts and/or other attachment mechanisms on inner walls and/or other difficult/impossible to access locations of the frame, the disclosed frames and related components include externally accessible connection features that can be easily accessed while being worn by the patient, allowing for the quick and convenient addition and/or removal of frame sections and/or components at virtually any location, including during out-patient office visits.

In various embodiments, temporary and/or reinforcement components are described that can be utilized to reinforce and/or replace sections of the modular frame, such as when section of the frame must be removed and/or reconfigured to allow access to a wound location. For example, if a patient wearing a modular frame develops a pressure sore or infection, it may be desirous to remove various frame components overlying the wound, as well as potentially remove bone connecting components, including Schanz Screws and/or Steinmann Pins, from the bone adjacent to the wound. In such a case, it may be desirous to attached additional rods or other support components to the frame to reinforce various frame locations, including locations that may be potentially weakened due to component removal for wound access. Once the wound has been treated (and the original and/or replacement frame members have been restored), the added reinforcement rods and/or other support components could be removed and/or repositioned, if desired.

BRIEF DESCRIPTION OF THE DRAWINGS

The drawings and the following description relate to preferred embodiments by way of illustration only. It should be noted that from the following description, alternative embodiments of the components and methods disclosed herein will be readily recognizable as viable alternatives that may be employed in one skilled in the art.

FIGS. 4A through 4C depict plan, bottom and side views of another exemplary embodiment of a fixation plate;

FIGS. 7A and 7B depict another exemplary embodiment of a composite plate structure formed from a first plate and a second plate FIGS. 8A and 8B depict another exemplary embodiment of an adapter plate;

FIGS. 13A and 13B depict perspective and cross-sectional views of an exemplary embodiment of a reinforced securement opening in a frame plate;

FIG. 14 depicts another exemplary embodiment of a reinforced securement opening in a frame plate;

FIG. 15 depicts a perspective view of another exemplary embodiment of a securement opening in a frame plate;

DETAILED DESCRIPTION OF THE INVENTION

Figure 1:
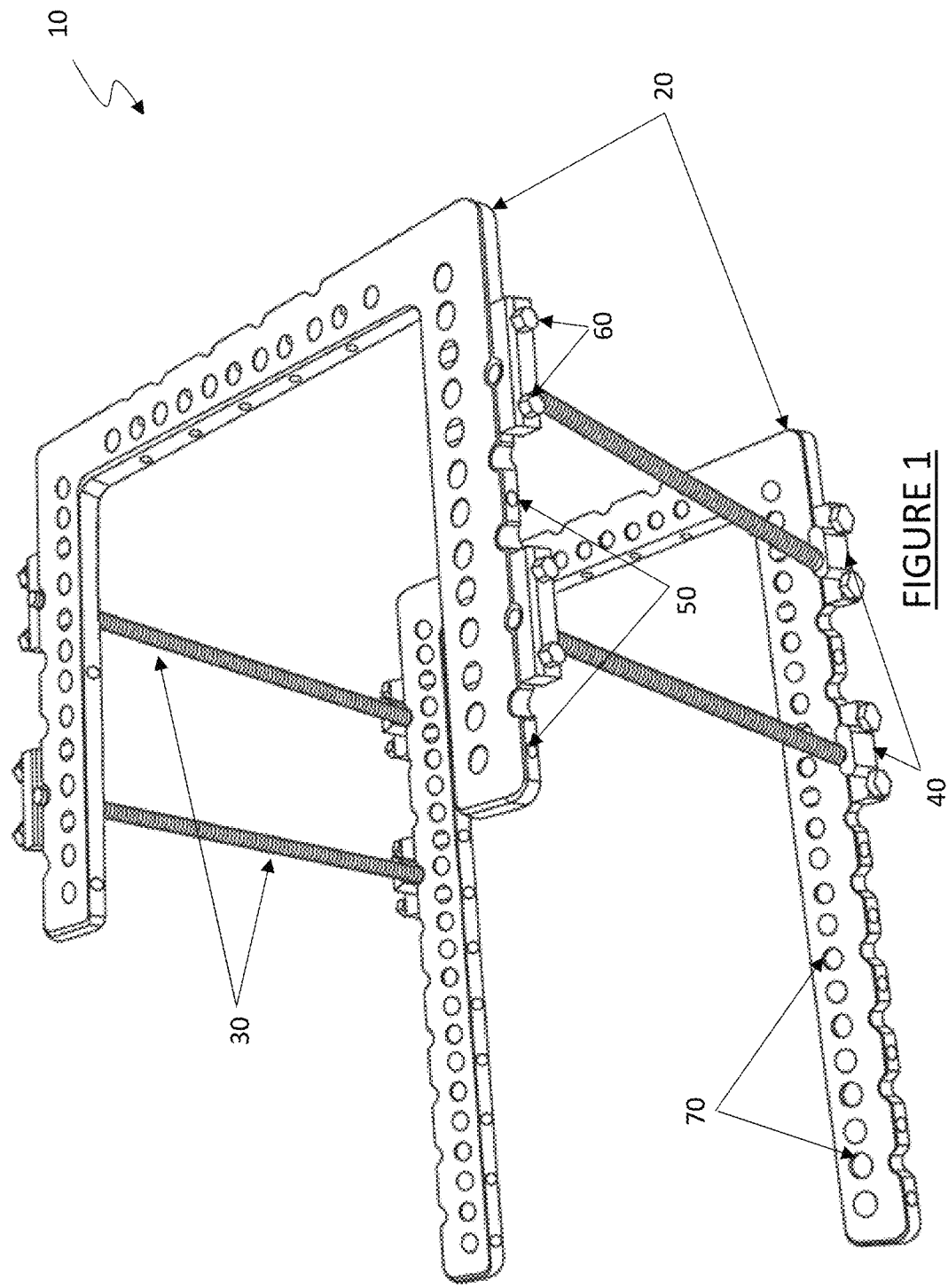
FIG. 1 depicts one exemplary embodiment of a fixation frame.

The disclosures of the various embodiments described herein are provided with sufficient specificity to meet statutory requirements, but these descriptions are not necessarily intended to limit the scope of the claims. The claimed subject matter may be embodied in a wide variety of other ways, may include different steps or elements, and may be used in conjunction with other technologies, including past, present and/or future developments. The descriptions provided herein should not be interpreted as implying any particular order or arrangement among or between various steps or elements except when the order of individual steps or arrangement of elements is explicitly described.

Orthopedic fixation systems as described herein generally include frame structures that surround and/or extend along one or more bones to allow for stabilization of a fracture and/or reconstruction of bones and/or surrounding tissue. The systems of the present invention can include a variety of components that can be selected for a desired level of stabilization. Systems of the present invention can include at least two main components: one or more support plates and interlocking spacer and support rods. As indicated herein, a support plate will generally extend around a region of the targeted anatomy, often extending transverse and/or angled relative to the anatomy, while the spacer and support rods typically extend parallel or along the anatomy. In various embodiments, bone-interface components (fixation pins, for example) that can assist in stabilizing a bone (e.g., tibia, fibula, femur or humerus), can be attached to the plates and/or rods in a variety of ways. As part of the embodiments disclosed herein, various frame components are disclosed, including plates, rings, struts, rails, and/or braces, as well as bone-interface components such as various types of orthopedic pins, rods, screws, shafts, wires, and the like that can connect to a bone, e.g., between a frame component and the patient's bone/fragment for positioning or reduction as described. Bone-interface components are commonly coupled to frame ring structures and can be coupled to various frame components, including plates, rings, struts, rails, arms, etc. The various frame components, for example, can be used by a healthcare provider to assemble the systems in a fashion to allow for varied levels of stabilization.

For use, the systems of the present invention can be generally used for medical procedures that involve fixation and/or reduction of a patient's bone, including limb stabilization. The orthopedic fixation systems of the present invention can be applied to treat various bones or fractures, including bones/fractures of both upper and/or lower limbs, such as a bone in the leg or the arm. A leg bone can include a femur, a tibia, a fibula, or a combination thereof. An arm bone can include a humerus, a radius, an ulna, or a combination thereof. In some embodiments, a segment of a bone can be treated using a device of the present invention. In certain embodiments, the orthopedic fixation systems of the present invention can also serve as reduction devices for a fractured or dislocated bone. For example, the systems can be configured to provide open or closed reduction. For open reduction, bone fragments are exposed surgically to assist in restoring a fracture or dislocation. Closed reduction can manipulate the bone fragments without surgical exposure.

In certain notable aspects, the various components and relationships therebetween can allow for increased portability and flexibility for stabilizing a bone, for example, in an outpatient setting and/or at the scene of an accident or other environments in which the ability to quickly assembly and/or easily modify the frame design can be particularly useful. The systems described herein can also provide a greater versatility in use because the systems can be assembled and/or modified to allow for different levels of stabilization of the bone. For example, in some situations, healthcare providers may desire more adjustable systems for mobility that can later be modified to increase stability upon arrival to a location that allows for such modifications, such as where an initial portability may be desired to keep the bone stabile before and/or during surgery in an operating room. As described herein, the disclosed embodiments can be assembled to include frame components that may allow for fixation or reduction of a bone in situations that involve more temporary, mobile stabilization or other situations that desirably provide greater stability that may be desired for some operating room situations, including components that may allow the fixation frame to be secured to a bed, a surgical table and/or some other support.

As described herein, the disclosed systems can include a multitude of frame components, such as plates (also commonly referred to as "rings") and spacer/support rods. The plates can be of any size and/or shape suitable for use with the systems, devices, and methods of the present invention. The plates can include full plates and/or partial plates, such as half or three-quarter plates, straight and/or curved sections or portions thereof, and/or angular C or U-shaped plates (as well as curved equivalents thereof, if desired). Various plates will desirably further include a variety of mechanisms for mounting the spacer/support rods and/or other bone-interface components. For example, plates can include holes (including internally threaded holes and/or hole portions) ribs, indentations, depressions, protrusions and/or other features that can be coupled with spacer/support rods and/or additional mounting components, such as brackets or other structures that allow for coupling with connectors to interface with bone. In certain embodiments, the plates can be removably and/or slidably coupled to allow removal and/or horizontal displacement of the plates in relation to a bone and/or other portions of the frame structures without greatly affecting the strength and/or support to the bone provide by the remaining frame elements. Once in a desired position, the plate and/or other frame components can be tightened and/or resecured to other frame elements in a desired new position and/or orientation.

In various embodiments, the spacer/support rods or struts used in the present invention may have any suitable dimension of size or shape to, for example, provide for stabilization and/or mounting of various bone-interface components or other frame components. Rods or struts can be elongate and substantially linear in shape or a whole or part of the rod/strut can be bent (e.g., angular and/or curved). In some embodiments, a strut can be a member of a set of struts, in which each strut can be the same size/shape or of different sizes/shapes. The set of struts can include struts of the same and/or different diameter, the same and/or different maximum (and/or minimum) length, and/or the same and/or different angular adjustability. Distinct struts, of the same or different size/adjustability, can be marked as distinct. For example, the struts may include indicia, such as alphanumeric characters, distinct colors, removable (or permanent) colored bands, etc. In some embodiments, the indicia can be used by a healthcare professional to choose specific struts having a desired shape and/or stiffness for a particular stabilization procedure. In certain embodiments, struts can also include one or more movable joints that can, e.g., permit relative (internal) translational or pivotal motion of portions the strut. In some embodiments, the joint can allow a twisting motion about an axis parallel to a long axis defined by the strut. In addition, a joint can also permit a bending motion(s) about an axis (or axes) transverse to the long axis of the strut. The joint may be a hinge joint, a ball-and-socket joint, and/or a combination thereof, among others.

The rods and/or struts can be secured by any suitable mechanism to plates and/or other fixation frame components of the present invention. For example, a strut can be fastened at several points along a set of plates. Alternatively, one strut can be coupled at one end to one plate and at the other end to a second plate. The locations and orientations of the struts in relation to plates, or other components, can be dependent on the particular application of the struts for stabilizing the bone in an orthopedic fixation system of the present invention.

If desired, additional support components, such as braces, can be coupled to the various fixation frame components so as to increase or decrease the stabilization level of the orthopedic fixation systems. In certain embodiments, the braces can provide additional stabilization support as well as to provide adjustment capability for a user. Suitable brace components can include rod supports, hinges, adjustment handles, joints, etc. The braces can have a configuration that can be adjusted in a variety of ways, such as in length, angle, height, etc. In some embodiments, the braces can include at least one joint or hinge to permit internal relative motion among various components of the brace. Other components, such as adjustment handles, can be configured to allow a healthcare provider to adjust the size and/or shape of the brace as well as the way the brace can couple with other system components.

In addition to the frame components, the present invention includes bone-interface components that can be connected to a bone. Suitable bone-interface components can include fixation pins, wires, screws, nails, plates, rods, bolts, staples, hooks, clamps, and the like, and/or various combinations thereof. The bone-interface components can extend into bone, through bone, and/or around bone, etc. Furthermore, the bone-interface components can be slidably engaged with bone and/or fixed in relation to bone (e.g., threaded into bone). In some embodiments, the bone-interface components can extend from a frame component, e.g., a plate or rod, to bone, or from a frame component to bone and then back to the same frame component. In other embodiments, a bone-interface component can extend from a frame component to bone and then to a different frame component. Each frame component can be connected to bone via the same or different type of mechanism.

In general, the frame components and/or bone-interface components can be coupled (e.g., permanently or removably coupled) to other components through a variety of ways. The coupling mechanisms for the systems of the present invention can generally include coupling mechanisms, such as fasteners, screws, nuts, brackets, and/or bolts, as well as other ways to attach various components, such as welding, gluing, tying, etc. In addition, plates can be removably and slidably coupled to various frame components. Fixing pins and/or wires can be independently and/or removably coupled to the plates and/or rods. Alternatively, the fixing pins and/or wires can be independently and/or removably coupled to other components that are coupled to the plates and/or rods. Coupling additional components to various parts of the assembly can depend on several factors, such as the bone needed fixation and/or reduction or, e.g., the placement of a fracture in the bone.

In one exemplary embodiment, shown in FIG. 1, a fixation frame 10 can include a plurality of elongated U-shaped plates 20 having substantially straight legs, the plates 20 attached to ends of a plurality of threaded rods 30. The rod ends are desirably secured by clamping plates 40 which are connected to threaded holes 50 which extend transversely through the walls of the plates 20, which in this embodiment are secured using threaded bolts or screws 60. In this embodiment the plate 20 and the clamping plates 40 can optionally include threaded walls which engage with and secure the threads of the rods 30, although in other embodiments the plate and the clamping plates could include compression or frictional engagement mechanisms to desirably secure the rods to the plates. A series of openings or holes 70 are also shown, which can be of the same of differing sizes and can be utilized to accommodate rods or other frame components, if desired.

In various embodiments, the plates 20 can include full plates and/or partial plates, such as straight plates, angle or half plates and/or three-quarter plates, as well as U-shaped plates (including straight and/or curved plates and/or portions thereof. The plates 20 will desirably include a variety of vertical and transverse holes for coupling additional components to the plates. Each plate can desirably be removably and/or slidably coupled to adjacent frame structures with one or more rods or struts that can, for example, be configured to provide load-bearing support. A plate can be attached to a strut with a fastening member, or the rod can include features (i.e., external threads) that can engage with internal structures (i.e., internal threading) in some or all of the holes or depressions. The struts could similarly be further coupled together by various fixation components or coupling members (i.e. trusses) which can, e.g., increase the stability of the device.

Figure 2:
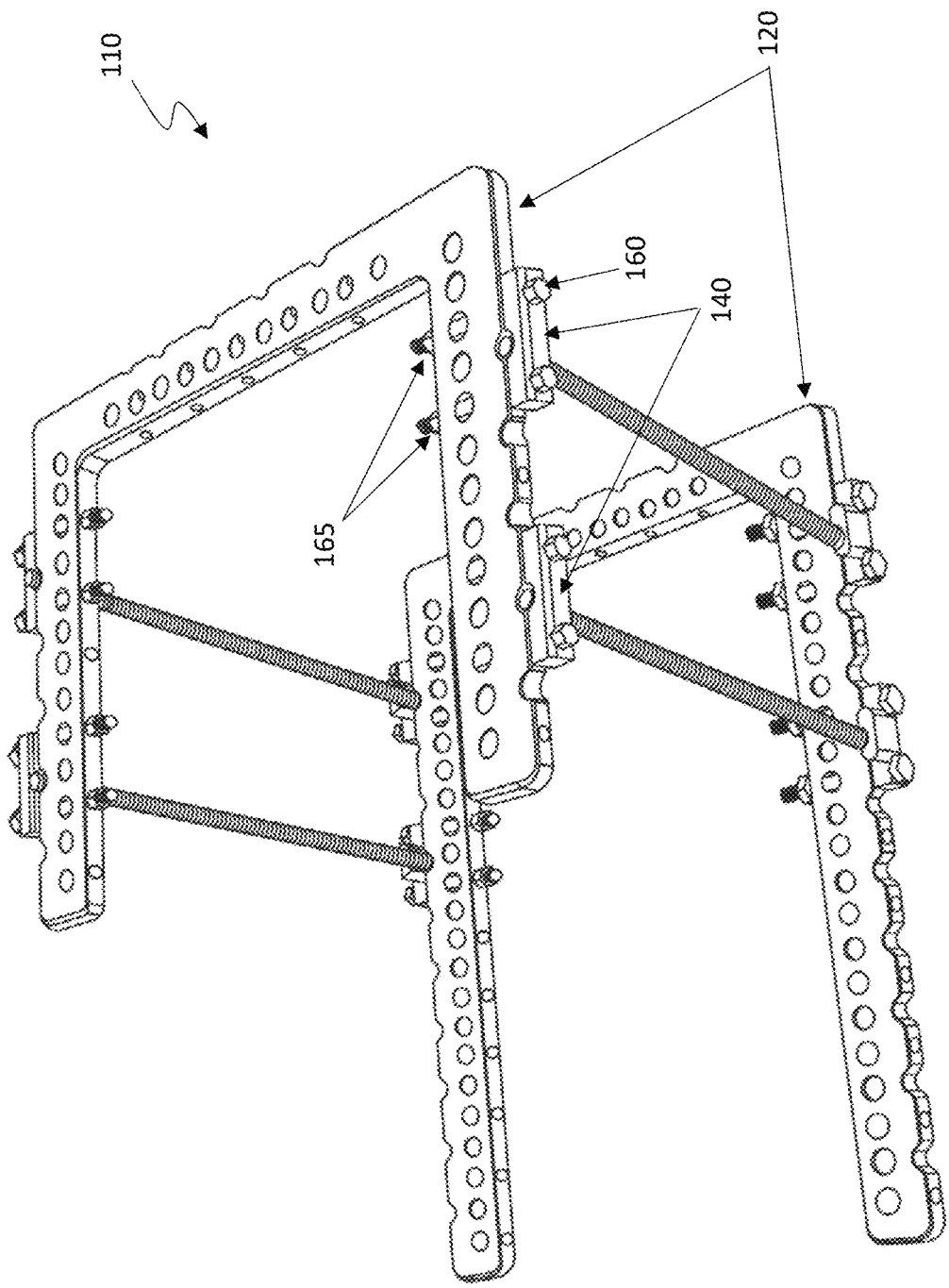
FIG. 2 depicts an alternative embodiment of a fixation frame.

FIG. 2 depicts another exemplary embodiment of a fixation frame 110 which includes many similar components as the frame of FIG. 1, but in which the clamping plates 140 are secured to the plates 120 using a threaded bolt 160 and corresponding internal nut 165. Such an arrangement may increase a holding strength of the clamp plate 140, but the presence of the internal nut 165 may be undesirable in some manner where it may rub against patient anatomy and/or interfere with additional components that may be positioned on the frame.

Figure 3A:
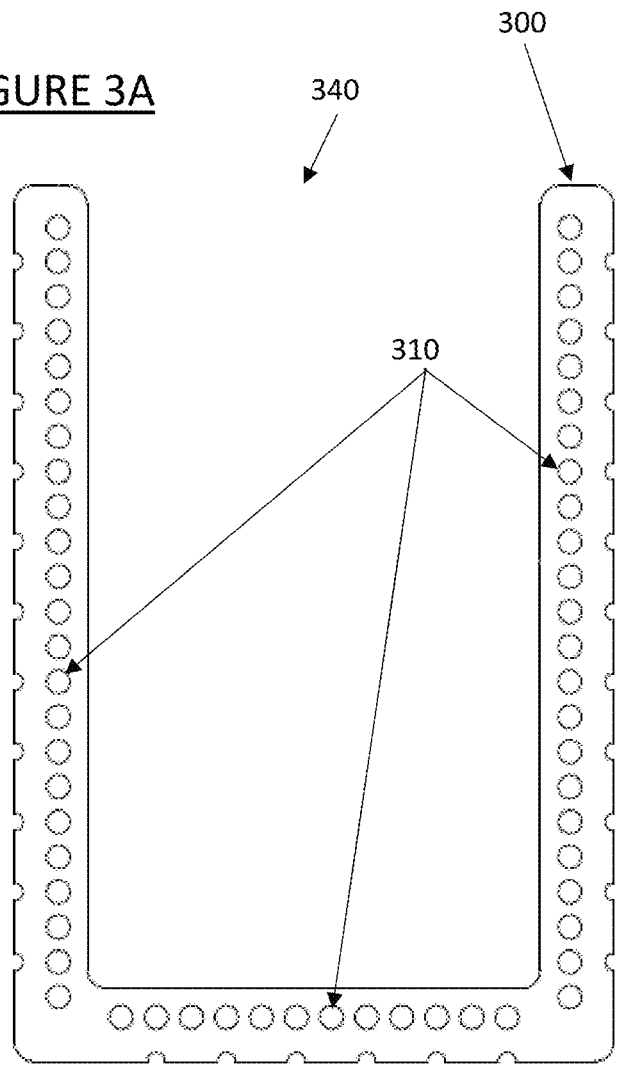
FIGS. 3A through 3C depict plan, bottom and side views of one exemplary embodiment of a fixation plate.
Figure 3B:
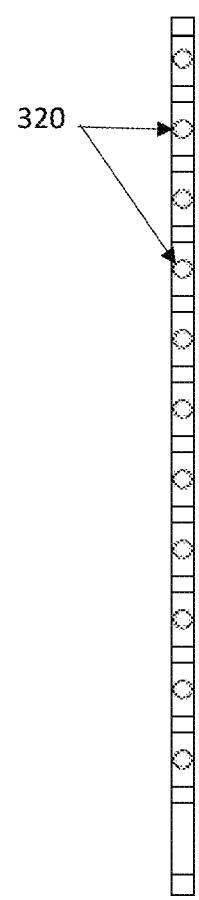
Figure 3C:
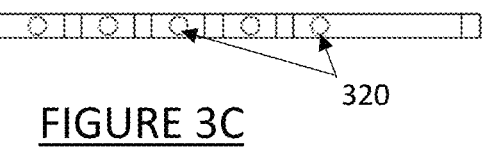

FIGS. 3A through 3C depict plan, bottom and side views of an exemplary fixation plate 300. In this embodiment, the plate 300 includes a top surface and a bottom surface, with a series of holes or opening 310 extending therethrough. If desired, some or all of the openings 310 may be internally threaded and/or of non-circular shape. The openings 310 may be cylindrical or conical or frustoconical or other cross-sectional shapes as desired. The openings 310 may be of the same or different sizes. The fixation plate will desirably also include a plurality of transverse openings 320 which extend through the side walls of the plate 300, some or all of which may be internally threaded or smooth, of non-circular or circular shape, or cylindrical or conical or frustoconical or other cross-sectional shapes, and may be of the same or different sizes—or various combinations thereof.

In use, the plate 300 desirably will be provided in a fixation frame kit containing a variety of different sized and/or shaped plates and other frame components. In use, the plate 300 can be desirably positioned around a limb or extremity (or other anatomy), with an open end 340 of the plate advanced over a treated limb (not shown), with the limb ultimately positioned within the recess 350 of the plate.

FIGS. 4A through 4C depict plan, bottom and side views of another exemplary fixation plate 400, this plate 400 being of a different shape and/or size to the plate 300 of FIGS. 3A through 3C, but with many similar features including openings formed therethrough.

Figure 5A:
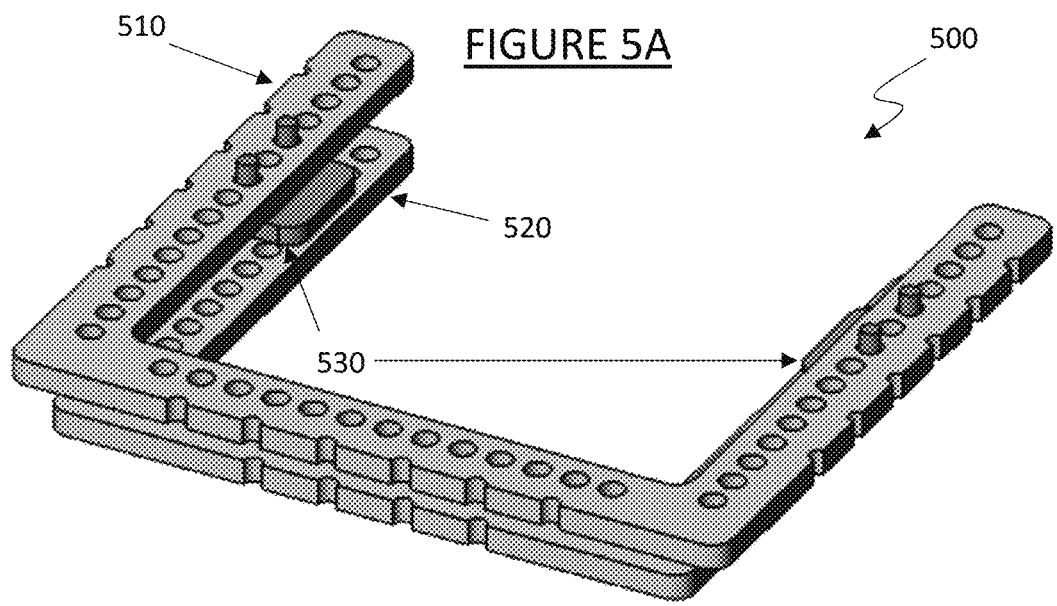
FIGS. 5A and 5B depict one exemplary embodiment of a composite plate structure formed from a first plate and a second plate.
Figure 5B:
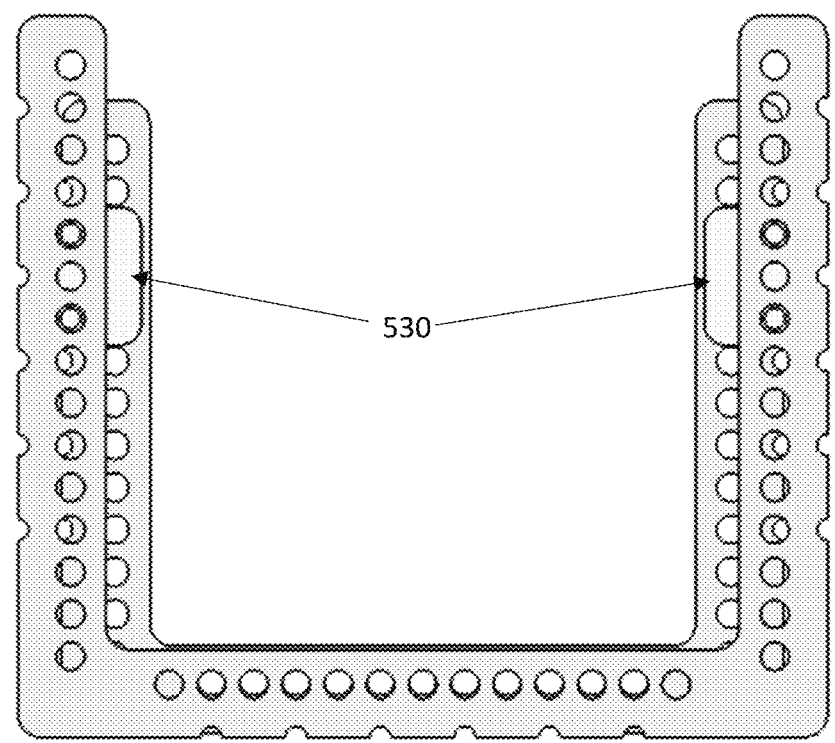
Figure 6A:
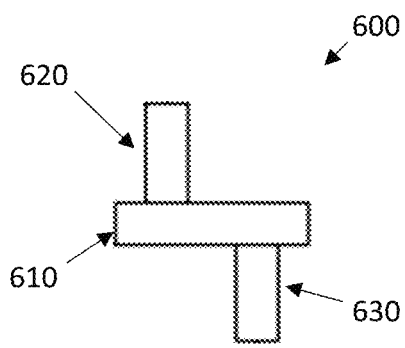
FIGS. 6A through 6D depict one exemplary embodiment of an adapter plate.
Figure 6B:
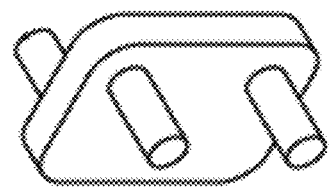
Figure 6C:
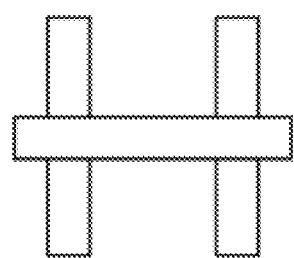
Figure 6D:
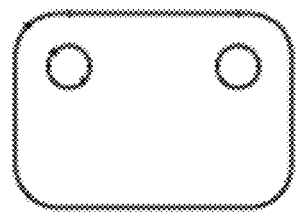

FIG. 5A depicts a composite plate structure 500 formed from a first plate 510 and a second plate 520, which are connected by a pair of adapter plates 530. In this embodiment, an upper section of a fixation frame (not shown) can be constructed using larger plates, while a lower second section of the fixation frame (not shown) can be constructed using smaller plates, with the composite plate structure 500 connecting the upper and lower sections together. Of course, in alternative embodiments some or all of the openings in the plates could be angled or tapered, and/or the connecting struts or rods could be curved, bent and/or otherwise deformed to accommodate the patient anatomy.

FIGS. 6A through 6D depict one exemplary embodiment of an adapter plate 600, which includes a flat plate body 610 with a pair of upwardly extending arms 620 and a pair of downwardly extending arms 630. If desired some or all of the arms 620 and 630 may be threaded or smooth, or any combinations thereof.

FIGS. 7A and 7B depict plan and side views of another alternative embodiment of a composite plate structure 700 formed from a first plate 710 and a second plate 720, with another embodiment of an adapter plate 800 connecting the first and second plates together. As best seen in FIGS. 8A and 8B, the adapter plate 800 can comprise a central body 810, which in this embodiment is formed in an x-shape (although other shapes can be used alternatively). An upwardly extending arm 820 and a downwardly extending arm 830 are also shown extending from the body, and these arms 820 and 830 can be threaded or smooth. In use, the arms of the adapter plate 800 can extend into and through the holes in the first and second plates, and a nut or other securement device can be attached to the arms, if desired, securing the plates together.

Figure 9A:
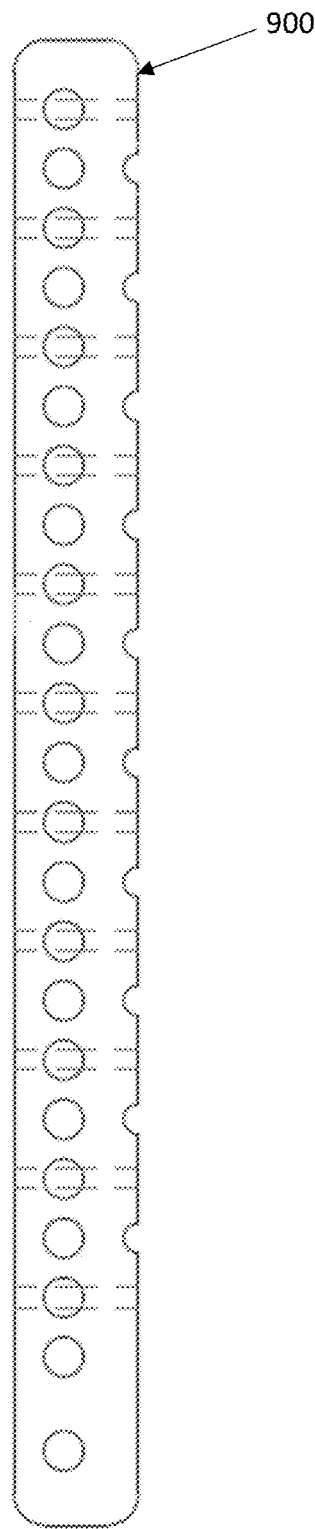
FIGS. 9A and 9B depict plan and side views of an exemplary embodiment of a straight plate.
Figure 9B:

FIGS. 9A and 9B depict plan and side views of another embodiment of a plate 900, which is depicted as a straight plate. In a manner similar to the plates previously described, some or all of the openings through the plate may be internally threaded, or of non-circular shape. The openings may be cylindrical or conical or frustoconical or other cross-sectional shapes as desired. The openings may be of the same or different sizes. The fixation plate will desirably also include a plurality of transverse openings which extend through the side walls of the plate, some or all of which may be internally threaded or smooth, of non-circular or circular shape, or cylindrical or conical or frustoconical or other cross-sectional shapes, and may be of the same or different sizes—or various combinations thereof.

Figure 10A:
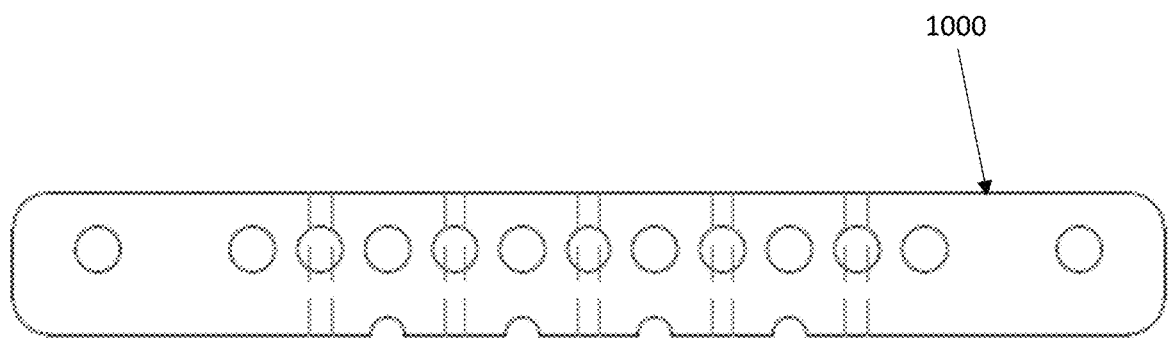
FIGS. 10A and 10B depict plan and side views of another exemplary embodiment of a straight plate.
Figure 10B:
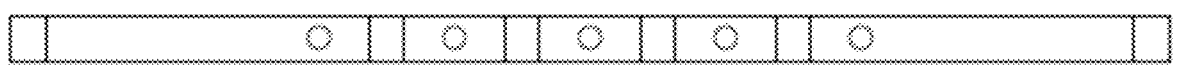

FIGS. 10A and 10B depict plan and side views of another embodiment of a plate 1000, which is depicted as a straight plate. In a manner similar to the plates previously described, some or all of the openings through the plate may be internally threaded, or of non-circular shape. The openings may be cylindrical or conical or frustoconical or other cross-sectional shapes as desired. The openings may be of the same or different sizes. The fixation plate will desirably also include a plurality of transverse openings which extend through the side walls of the plate, some or all of which may be internally threaded or smooth, of non-circular or circular shape, or cylindrical or conical or frustoconical or other cross-sectional shapes, and may be of the same or different sizes—or various combinations thereof.

Figure 11A:
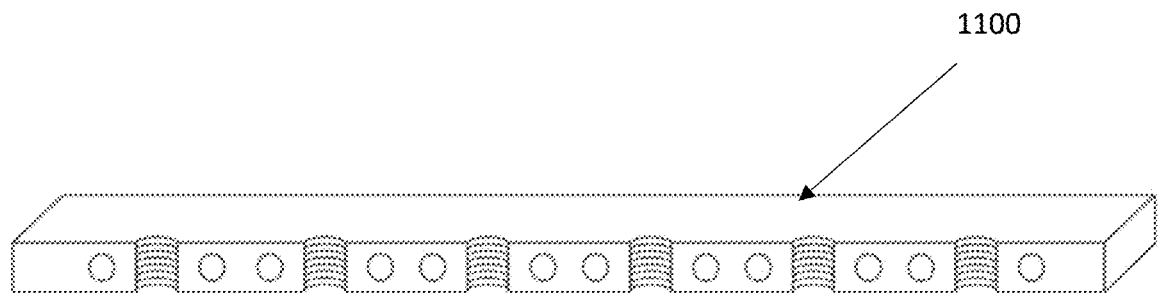
FIGS. 11A and 11B depict perspective views of another exemplary embodiment of a fixation frame plate.
Figure 11B:
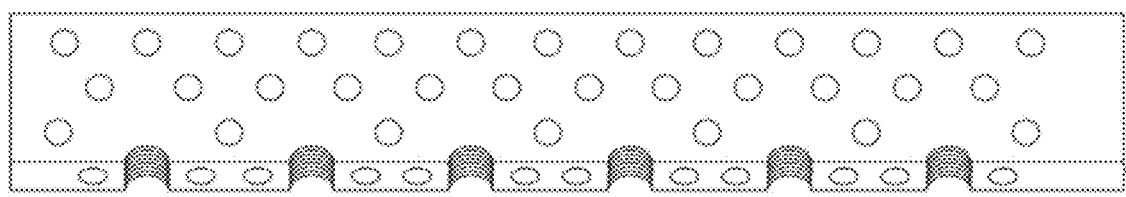
Figure 12A:
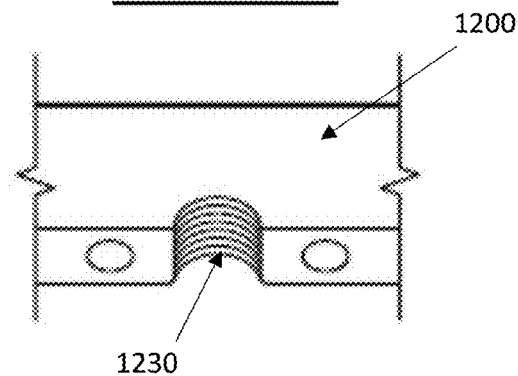
FIGS. 12A through 12E depict various views of an exemplary frame plate, a clamping plate and a threaded rod that form components of a fixation frame.
Figure 12B:
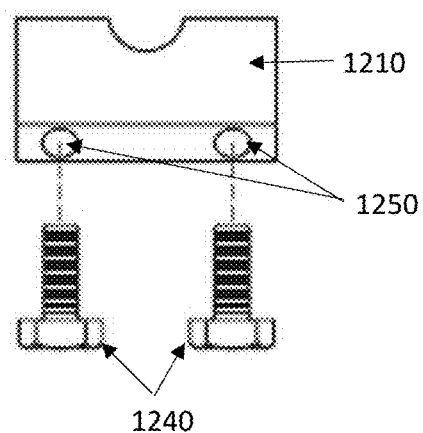
Figure 12C:
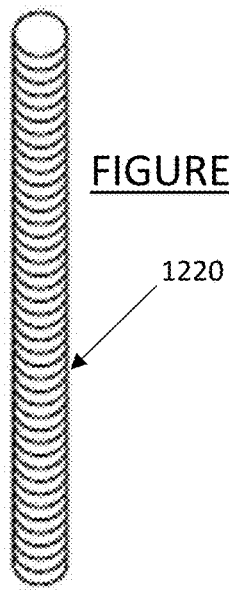
Figure 12D:
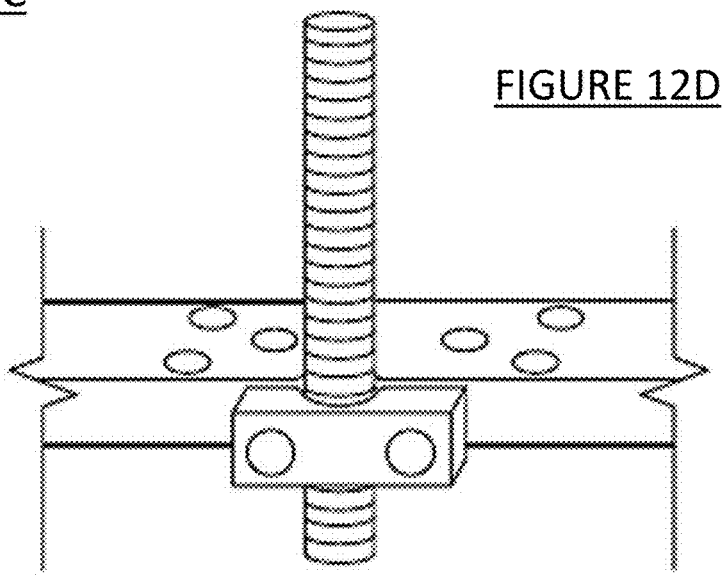
Figure 12E:
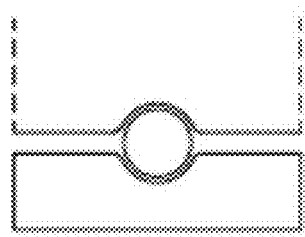

FIGS. 11A and 11B depict perspective views of another exemplary embodiment of a fixation frame plate 1100, which includes many similar features to the plates previously described, including where some or all of the openings through the plate may be internally threaded, or of non-circular shape. The openings may be cylindrical or conical or frustoconical or other cross-sectional shapes as desired. The openings may be of the same or different sizes. The fixation plate will desirably also include a plurality of transverse openings which extend through the side walls of the plate, some or all of which may be internally threaded or smooth, of non-circular or circular shape, or cylindrical or conical or frustoconical or other cross-sectional shapes, and may be of the same or different sizes—or various combinations thereof. In this embodiment, the plate 1100 includes a series of side holes or depressions 1110 which are internally threaded. Desirably, these threads could engage with an externally threaded rod and clamping plate (such as shown in FIG. 1 and FIG. 2).

FIGS. 12A through 12E depict various views of an exemplary frame plate 1200, clamping plate 1210 and threaded rod 1220 that form components of a fixation frame. In this embodiment, the threaded rod 1220 can desirably be slid laterally into the threaded depression 1230 in the frame plate 1200, and then the clamping plate 1210 can be placed over the rod 1220, and then fixation bolts 1240 can be inserted into corresponding thread plate holes 1250 and tightened, resulting in the construction of FIGS. 12D and 12E. If a physician desires to subsequently move the plate for some reason, it is not necessary to rotate the rod or remove other section (not shown) of the fixation construct— the physician need merely loosed the fixation bolts and the clamping plate can be removed and the rod freed from engagement with the threaded teeth of the plate 1200. Similarly, once a new positioned has been attained, the clamping plate can be retightened and the threaded rod locked in the new desired position without requiring adjustment of any other frame components.

FIGS. 13A and 13B depict perspective and cross-sectional views of an exemplary embodiment of a reinforced securement opening in a frame plate 1300. In this embodiment, a locally thickened section 1310 of the plate 1300 can be provided, with an internally threaded portion, which can desirably provide additional threaded engagement with a threaded rod or strut—dramatically increasing the "pull out" and "push through" strengths of the coupling (i.e., with the increased number of engaging threads) as well as potentially stiffening the rod relative to the plate (i.e., reducing the potential for the rod to "toggle" relative to the fixation plate). FIG. 14 depicts another exemplary embodiment of a reinforced securement opening in a frame plate 1400, which in this embodiment includes both an upward extending thickened portion 1410 and a downwardly extending thickened portion 1420, with respective internal threading provided therein. This embodiment can further increase the "pull out" and "push through" strengths of the coupling (i.e., with the increased number of engaging threads) as well as potentially stiffening the rod relative to the plate (i.e., reducing the potential for the rod to "toggle" relative to the fixation plate).

FIG. 15 depicts a perspective view of an exemplary embodiment of a securement opening 1510 in a frame plate 1500 which allows for some malalignment or "toggle" between a fixation rod (not shown) and the plate 1500 when a compression plate (not shown), optionally having complimentary design features, is secured to the plate 1500. In this embodiment, an upper end 1520 of the opening and a lower end 1530 of the opening are enlarged relative to the rod, which can allow the rod to angle somewhat relative to the plate (i.e., be not perpendicular to the plate)—up to 10 or 15 degrees in some embodiments. While a threaded central portion 1540 of the opening is depicted, alternative embodiments could include smooth or roughened wall surfaces to allow rod retention using friction or compression forces, if desired.

Figure 16A:
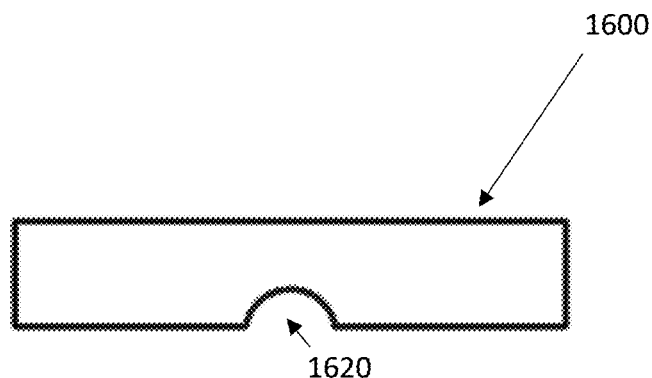
FIGS. 16A and 16B depict plan and side views of another exemplary embodiment of a compression plate.
Figure 16B:
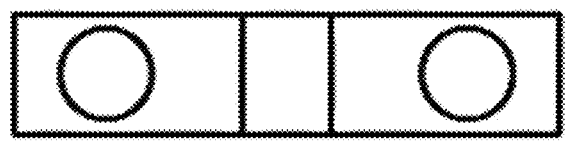
Figure 17A:
FIGS. 17A and 17B depict plan and side views of another exemplary embodiment of a compression plate.
Figure 17B:
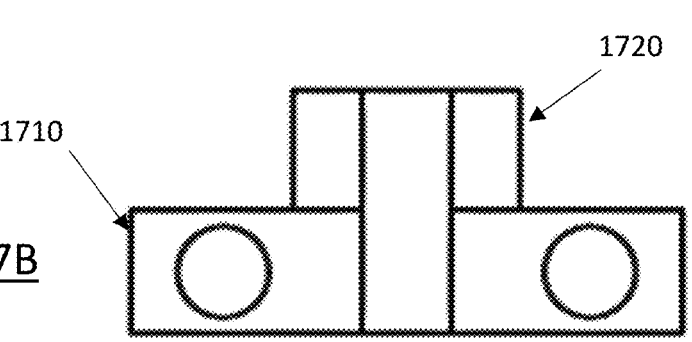

FIGS. 16A and 16B depict plan and side views of another exemplary embodiment of a compression plate 1600. In this embodiment, a depression or semi-circular opening 1620 can be provided to engage with a rod (not shown). If desired, the opening 1620 can have a smaller diameter than the rod to improve the "bite" or engagement with the rod (which could similarly include an opening in the fixation plate which is smaller than the rod, if desired). In alternative embodiments, the central threaded opening could comprise a roughened or textured surface which engages frictionally with a rod. FIGS. 17A and 17B depict plan and side views of still another exemplary embodiment of a compression plate 1700 In this embodiment, the plate 1700 includes a base body 1710 and an upwardly extending support arm 1720, which can desirably engage with a rod or other structure to impart additional rigidity and/or stability to the coupling, potentially increasing the strength and/or rigidity of the full frame construct in a desired manner.

Figure 18:
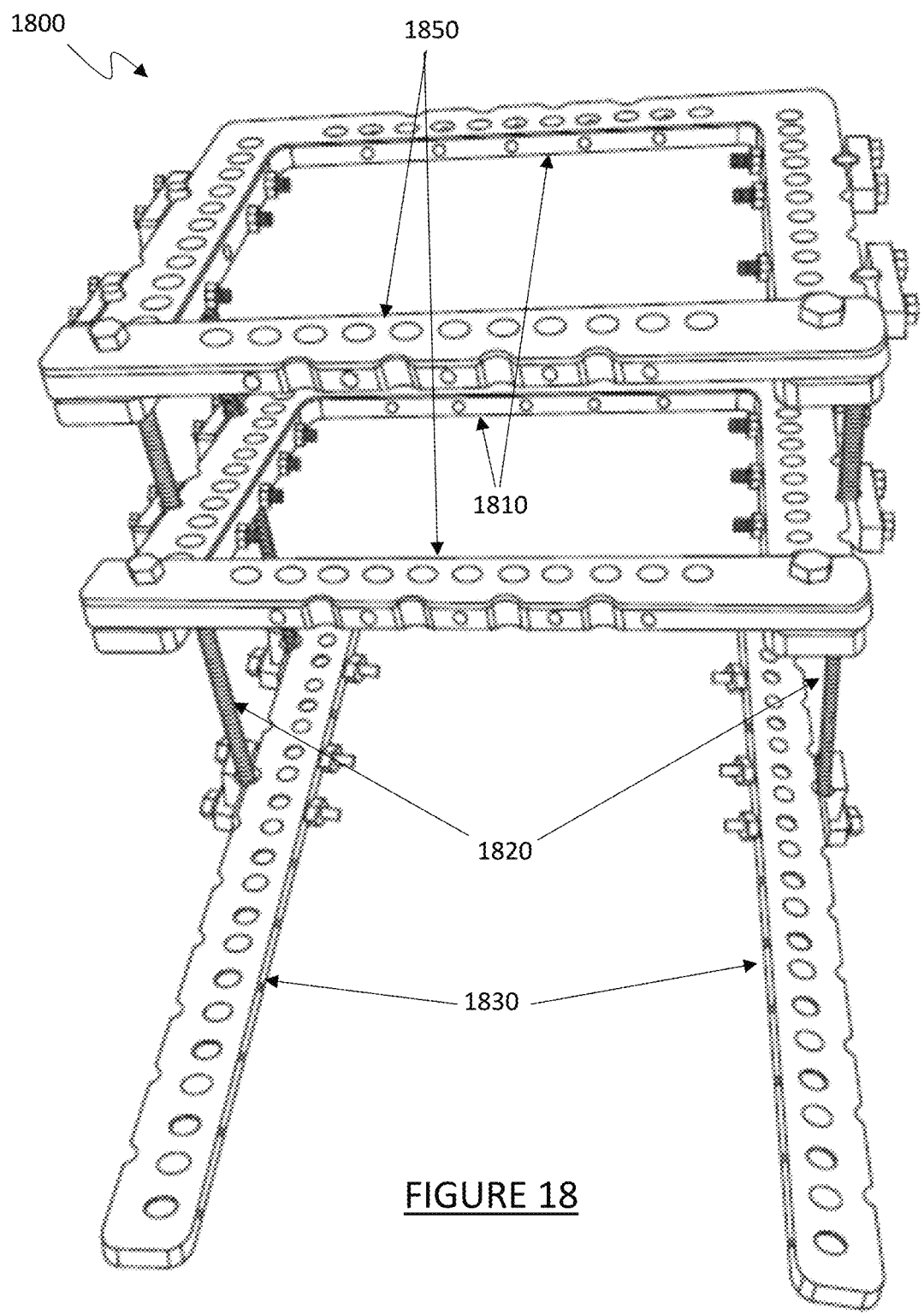
FIG. 18 depicts a perspective view of another exemplary embodiment of a fixation frame.

FIG. 18 depicts a perspective view of another exemplary embodiment of a fixation frame 1800, which includes many similar components as the frames of FIG. 1 and FIG. 2. In this embodiment, a pair of U-shaped plates 1810 are secured together by struts 1820 and various additional components, along with a pair of straight plates 1830. In addition, the open end of each of the U-shaped plates 1810 is secured closed by a straight plate 1850. Such a construct is extremely strong and rigid, and also requires a minimal number of component parts, rendering the construct relatively lightweight and inexpensive as compared to traditional frame designs.

Figure 19:
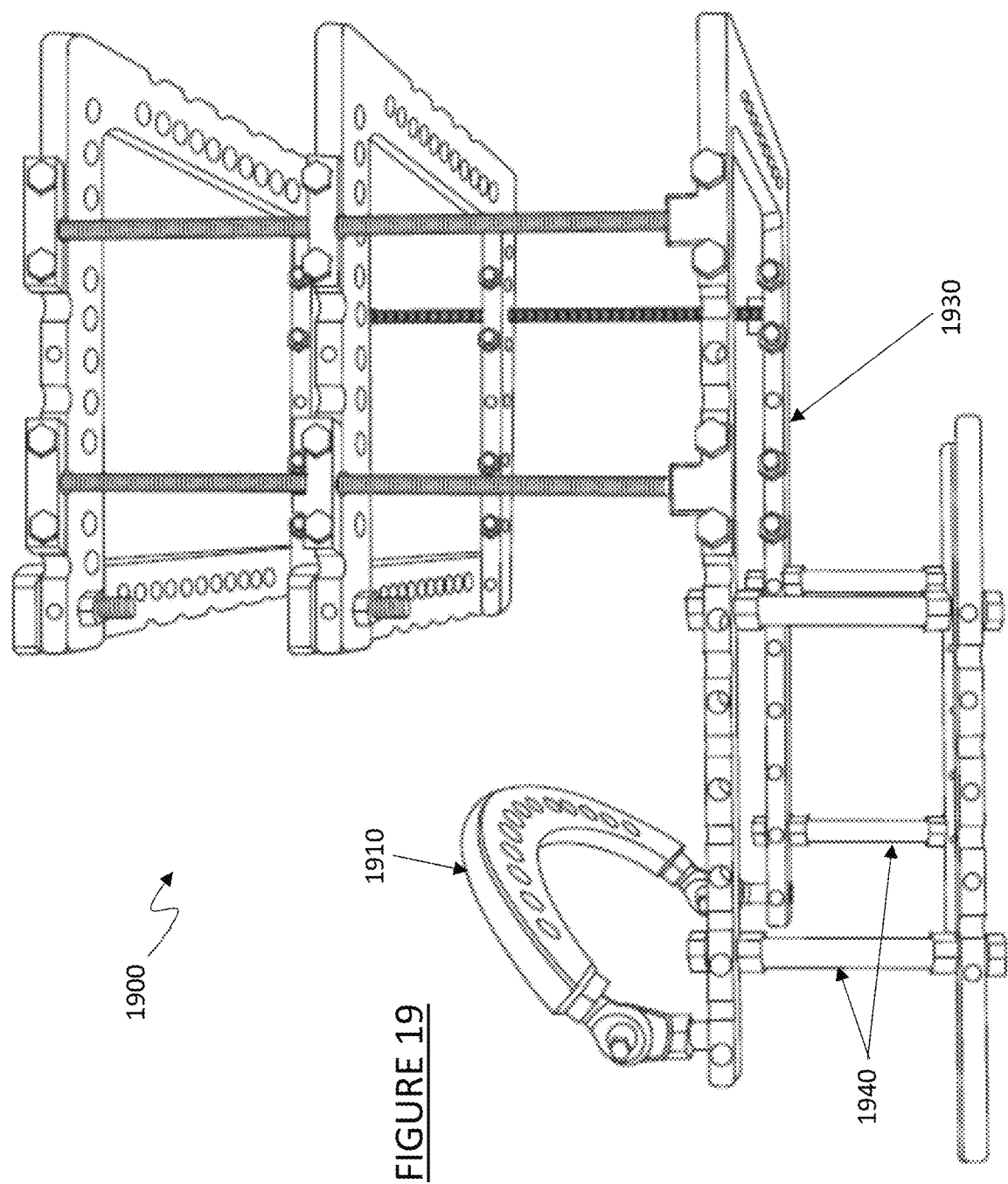
FIG. 19 depicts a perspective view of another exemplary embodiment of a fixation frame.

FIG. 19 depicts a perspective view of another exemplary embodiment of a fixation frame 1900, which includes many similar components as the frame of FIG. 18. In this embodiment, a curved plate 1910 is positioned at an end of a U-shaped plate 1930, with additional struts 1940 and plates extending outward from an opposing side of the U-shaped plate 1930.

Figure 20:
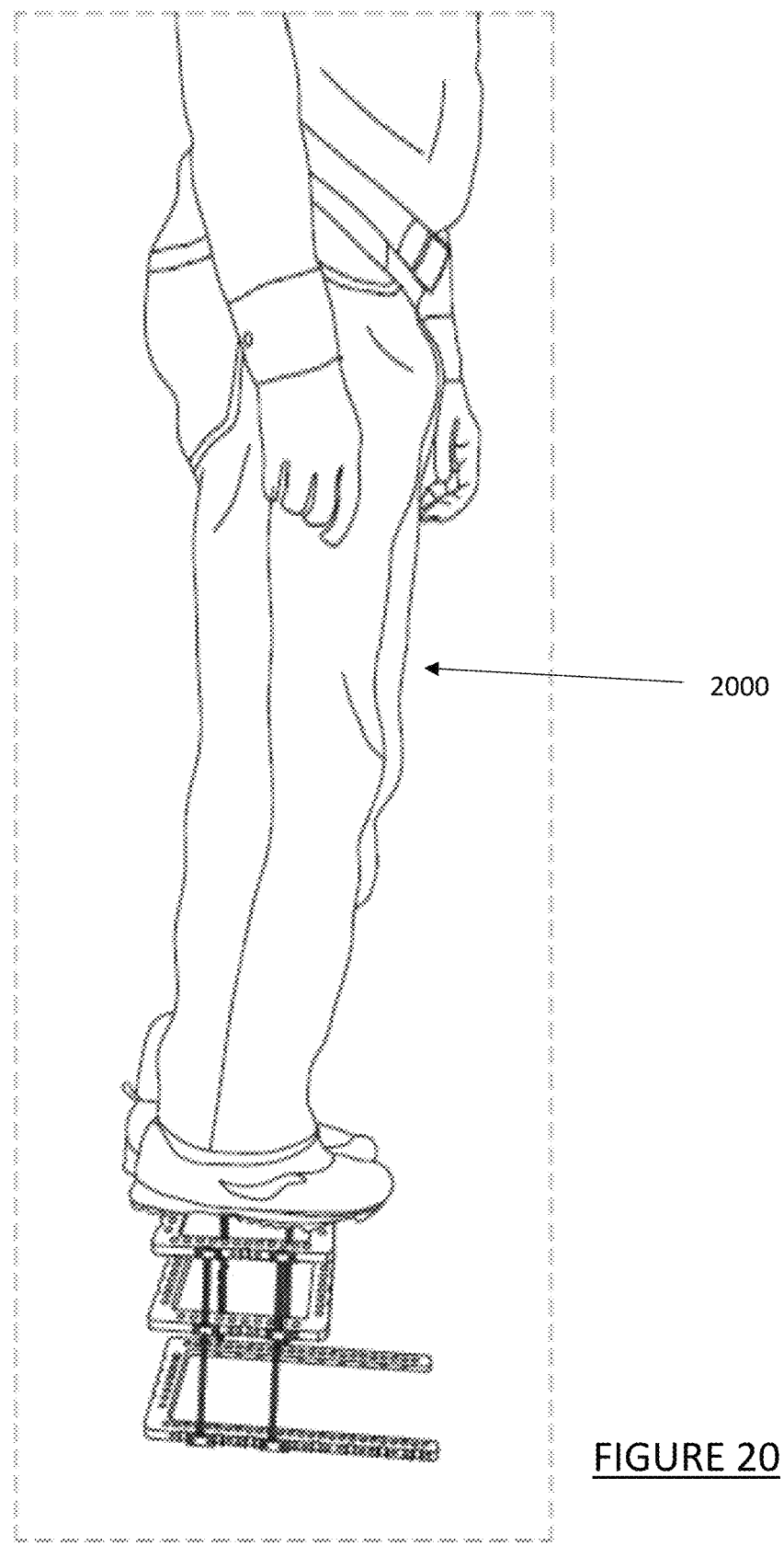
FIG. 20 depicts the fixation frame of FIG. 18 supporting the weight of an adult male.

FIG. 20 depicts the fixation frame of FIG. 18 supporting the weight of a fully grown adult male 2000, which has been adapted from an actual photograph of the same. This image aptly demonstrates the extreme strength and rigidity of the disclosed fixation frame—even where a minimal number of components is provided.

Figure 21A:
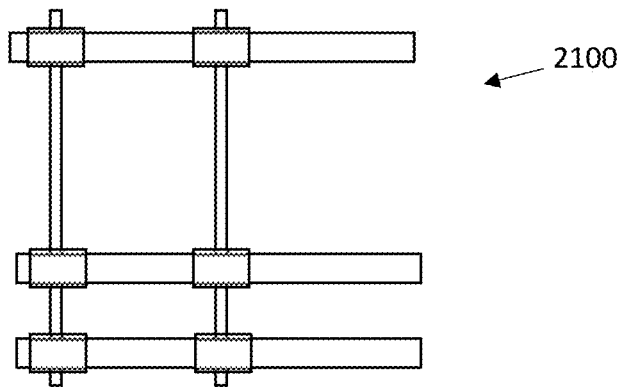
FIGS. 21A through 21D depict various exemplary fixation frame constructs that can be created using various components described herein.
Figure 21B:
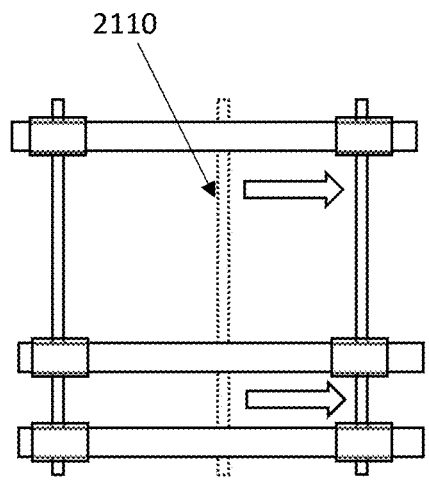
Figure 21C:
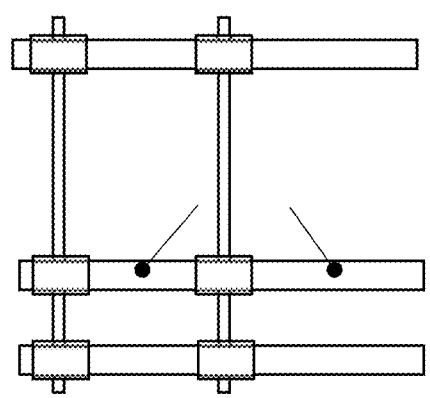
Figure 21D:
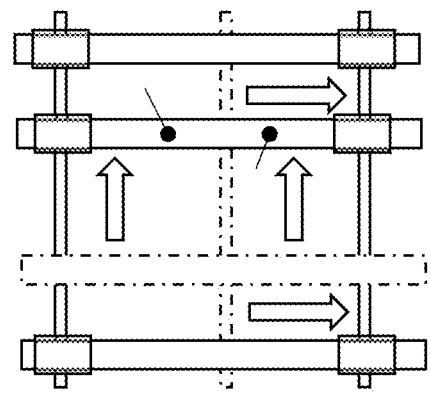

FIGS. 21A through 21D depict various exemplary fixation frame constructs that can be created using the various components and teachings described herein. FIG. 21A depicts a side view of an exemplary fixation frame 2100 that can be utilized on a patient. If a frame component obstructs a portion of the extremity or other anatomical feature in an undesired manner, the physician can loosen one or more individual components of the frame 2100, and reposition that component (i.e., a rod or strut 2110, as shown in FIG. 21B) to a new location (see phantom rod and arrows depicting movement of the component), where the component can be retightened in the new location without compromising the fixation or strength of the frame during such manipulation—thereby allowing the physician to access the wound for treatment, even allowing the placement of a negative pressure wound therapy device (i.e., "wound vac"), if desired. Similarly, if fixation pins 2130 or other bony attachment points (or frame components) require manipulation or repositioning from the positions shown in FIG. 21C, the frame members and/or fixation pins can be moved in a similar manner (see FIG. 21D) without affecting other fixation provided by the frame during such movement. In this way, portions of the frame and/or other support structures can be modified without comprising or affecting the support and fixation concurrently provided by the remainder of the frame, thereby allowing unfettered access virtually all of the patient's anatomy in a desired manner.

Figure 22A:
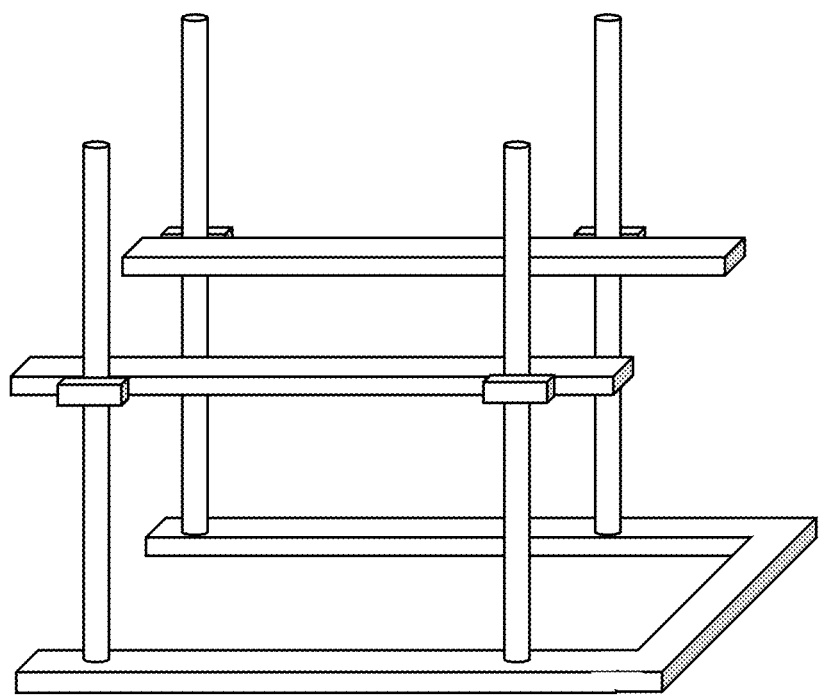
FIGS. 22A through 22C depict one exemplary method of constructing a fixation frame.
Figure 22B:
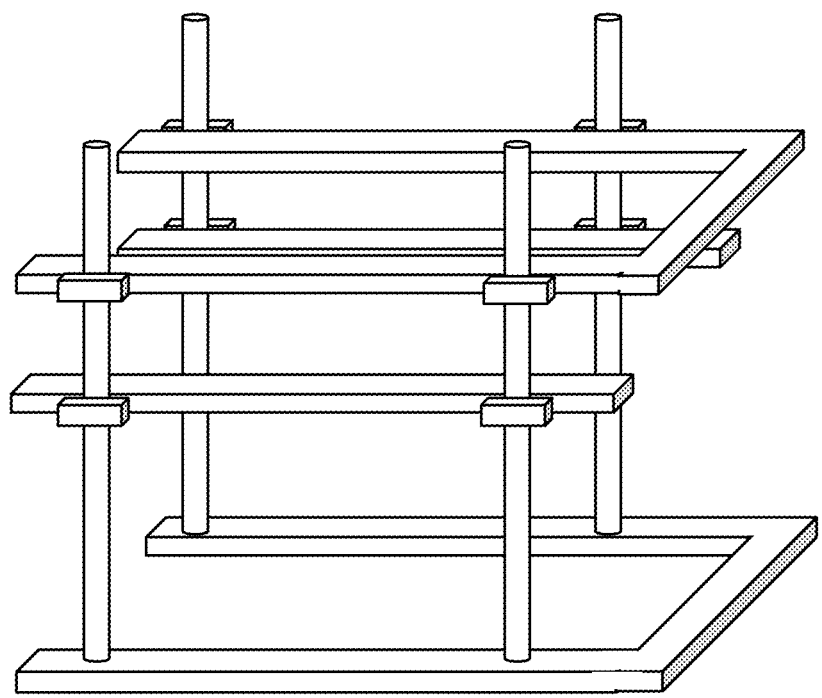
Figure 22C:
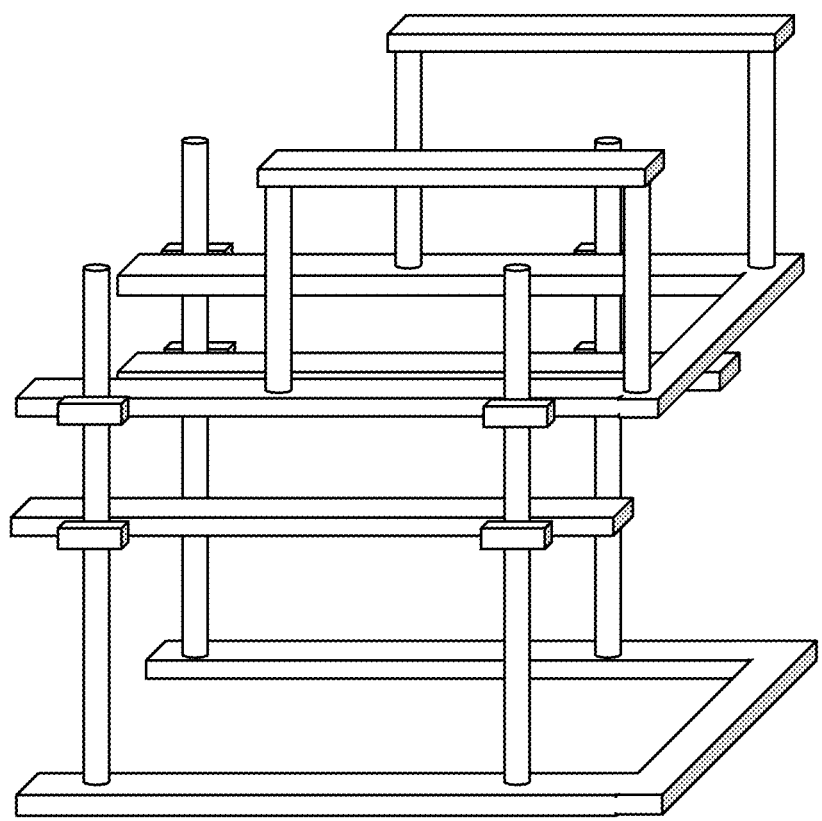

FIGS. 22A through 22C depict one exemplary method of constructing a fixation frame in accordance with various teaching of the present invention. As best seen in FIG. 22A, a two-level frame can be initially constructed and then placed around a patient's extremity (not shown). FIG. 22B depicts the frame with additional levels that can be added to the central support struts or other members of the existing frame as desired. FIG. 22C depicts the frame with an additional offset upper level secured above the existing frame members—the frame can continue to be modified as desired by the physician.

Figure 23A:
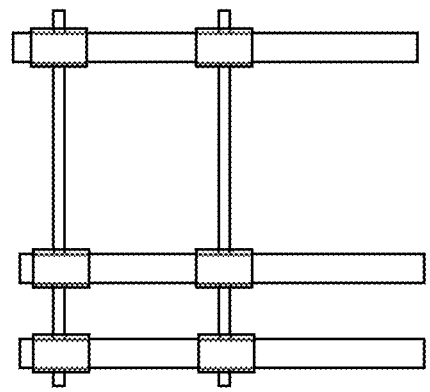
FIGS. 23A and 23B depict opposing lateral and medial sides, respectively, of an exemplary non-symmetrical fixation frame.
Figure 23B:
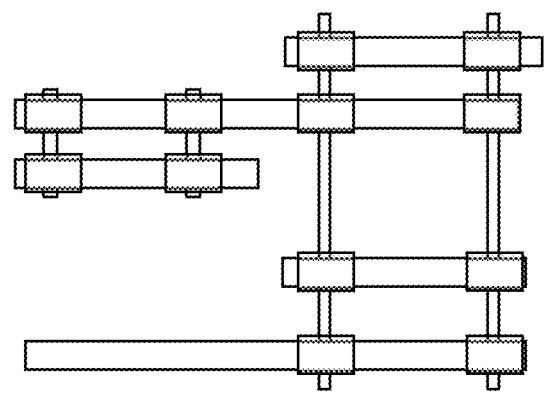

If desired, and depending upon anatomical considerations and/or physician preference, the opposing sides of a fixation frame may be symmetrical and/or non-symmetrical. For example, the side views of a frame may be substantially mirror images, or the side views can be different, such as depicted in FIG. 23A (a lateral view of a frame embodiment) and FIG. 23B (a medial view of the same frame embodiment). In this way, the frame can be particularized as necessary and/or desired.

Figure 24A:
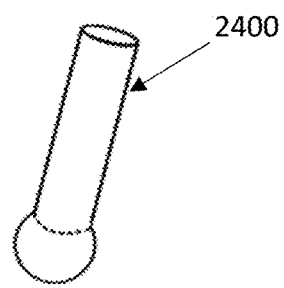
FIGS. 24A through 24C depict an exemplary embodiment of a variable angle rod connector.
Figure 24B:
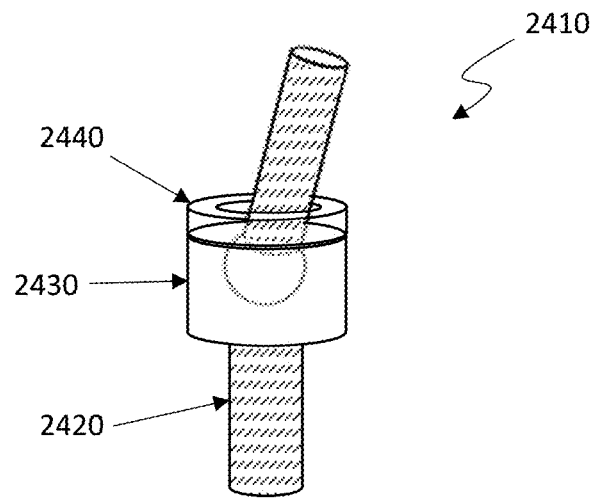
Figure 24C:
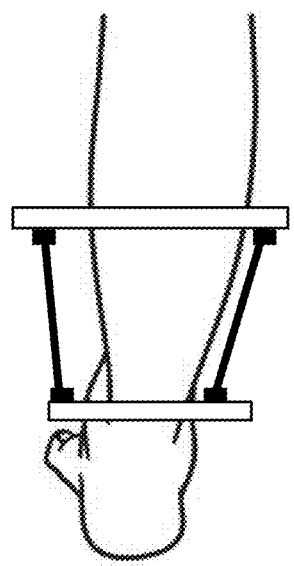

FIG. 24A depicts one alternative embodiment of a variable angle rod connector 2400 which fits within a corresponding recess in a swivel rod locking mechanism 2410 (see FIG. 24B) which includes a lower rod 2420, a cylindrical body 2430 and a locking compression cap 2440. In use, the swivel rod connector can facilitate off-axis attachment of a rod or strut in a fixation frame construct, such as depicted in FIG. 24C.

While the various embodiments described herein include more squared and/or rectangular (i.e., more angular) designs for fixation plates and/or other components, it should be understood that virtually any polygonal shape (and/or curved, oval and/or circular shapes) as well as combinations thereof could be useful for the various plates and/or other components, including triangular, pentagonal, hexagonal, septagonal, octagonal and/or rounded shapes, if desired. In some embodiments, square and/or rectangular system components may be easier to upsize and/or accommodate a variety of modular components, and may also be less expensive to manufacture. Moreover, the use of flat, angular and/or squared components can significantly reduce the require diameter of the fixation frame and/or allow the fixation frame to lay flat upon the one or more sides, which can be much more comfortable for the physician and/or wearer. In addition, there is typically more room underneath a squared frame between the frame and skin surface to accomplish dressing changes, as well as more space to modify dressings and/or add to dressings, as well as accommodate other items and/or equipment. This may be particularly useful for patient with obese legs or large calves, wherein the physician can shift the frame posterior (unlike rounded frames which are typically centered on the limb axis). Moreover, a squared frame design facilitates the use of offset rods and/or rod connectors, whereas offset of a rounded system would typically tilt the components of a round frame design in an unwanted manner.

In addition, the incorporation of flattened and/or angular plate components allows the use of a wide variety of clamp designs and/or other components to assemble the fixation frame—including the use of components of different sizes and/or shapes in a single construct. Various clamp designs can be utilized on a single level and/or frame member, which allows for many different ways to bolt or otherwise connect different size components together, which is not easily accomplished with many rounded fixation systems.

The various fixation frame designs disclosed herein allow for an open end of the square/rectangle of the plate to be positioned pointed forward, to either side or backward, as desired, with this opening being easy to close off with a straight plate or similar bar to prevent patient access and/or increase stability of the construct. The current concepts can optionally bring a foot rectangle to a square up the leg, desirably with a similar safety profile as current foot plates and related support component designs have shown. In addition, with the disclosed designs a caregiver can slide the square/rectangular plates forward or rearward (i.e., cephalad or caudad along a lower limb) to desirably accommodate leg size, dressings and/or other fixation equipment. In addition, squared and/or rectangular systems can accommodate components that are offset relative to a central longitudinal axis of the frame, and the various components can be upsized easier than with rounded systems.

If desired, the disclosed frame designs can optionally accommodate curved components such as c-shaped and/or u-shaped plates as a main level component (See FIG. 23), with opposing flat and/or C/U-shaped components to optionally close off the "box" on each level. In fact, various designs could incorporate rounded and/or curved sections, including rounded frame members (i.e., to create D-shaped frame members, for example) and/or curved support rods between frame sections. In a similar manner, the various components described herein could potentially accommodate and/or attach to components from other fixation systems, including rounded systems, if desired.

The various fixation frame components, including squared frame components, can be utilized to better "space out" the connecting rods and/or struts (including the use of rods in corners of squared frame sections), allowing a physician to change rod locations in office and/or much easier to add levels in the office or in surgery on a frame already on a patient. Moreover, the disclosed embodiments are faster to assemble and disassemble than existing designs, allow faster dressing changes, and these design also require significantly fewer parts.

In addition to easy of assembly, the disclosed frame designs desirably include a variety of features to allow frame components to be added and/or removed from the frame with little disruption to adjacent frame members. For example, current frame designs typically include rods and numerous nuts on inside surfaces of frame, with nuts on the ends of rods. In order to disassembly and/or modify these frame components, a surgeon or physician must unscrew all the nuts at both the top and bottom of a rod before rod removal can be accomplished. Moreover, if a nut or other component goes missing, it may be necessary to rebuild the entire frame to accommodate the missing components, and it is typically difficult to add frame sections in an out-patient environment.

The presently disclosed embodiments will desirably obviate the need for multiple assistants during frame placement and/or assembly. During a current surgical procedure, a surgeon will often utilize an assistant or folded and stacked towels, etc., to hold the patient's leg in a desired position and/or orientation within the frame to facilitate assembly. However, with the currently disclosed designs, the physician can optionally utilize removable supports or other features that can be attached to frame sections that can also be removed at the end of frame assembly. The current design also allows a physician to use one of more openings to guide pin placement and/or drill placement into patient anatomy (i.e., drill or obdurate through hole in frame). Moreover, the disclose designs incorporate a much higher number and distribution/orientation of pin positions than provided by current frame designs, which allows a physician to move rods and/or other components to allow pin positions and/or other anatomical features to be exposed in a desired manner.

One or more structures as described herein may be provided in the form of a kit. A kit may be assembled for portability, facilitating use in a surgical setting, and the like. A kit can typically include various components of an orthopedic fixation system of the present invention, and the orthopedic fixation system may be provided in a fully assembled, partially assembled, or non-assembled configuration. As indicated, a device of the present invention may be configured or of a designed such that one or more components of the fracture reduction system have a limited or single use, or are replaceable. A kit may include pre-sterilized components or device(s), as well as sterilized packaging. The components of the present invention may be sterilized (and will generally be sterilizable) by any of the well-known sterilization techniques, depending on the type of material. Suitable sterilization techniques include heat sterilization, radiation sterilization, chemical/gas sterilization, and the like.

In yet other embodiments, the present invention provides methods of using the devices and assemblies described herein. In an exemplary embodiment, the present invention provides a method of using an orthopedic fixation system can include modifying the fixation device in an outpatient or transportation setting while the patient's bone is immobilized with the fixation device.

Structures, devices, and assemblies of the present invention should not be limited to any particular construction materials or compositions. Materials and compositions of the invention can include any variety of metals, alloys, polymers, and the like, alone or in combination, that are commonly used or generally suitable for use in medical or surgical applications. Devices and components thereof may be made from conventional non-absorbable, biocompatible materials including stainless steel, titanium, alloys thereof, polymers, composites and the like and equivalents thereof. The use of lighter materials such as high strength metals, plastics and/or ceramics will desirably allow a square frame to have equivalent and/or lighter weight than a corresponding rounded frame and its components.

The specific dimensions of any of the orthopedic fixation systems, assemblies, and components thereof, of the present invention can be readily varied depending upon the intended application, as will be apparent to those of skill in the art in view of the disclosure herein. Moreover, it is understood that the examples and embodiments described herein are for illustrative purposes only and that various modifications or changes in light thereof may be suggested to persons skilled in the art and are included within the spirit and purview of this application and scope of the appended claims. Numerous different combinations of embodiments described herein are possible, and such combinations are considered part of the present invention. In addition, all features discussed in connection with any one embodiment herein can be readily adapted for use in other embodiments herein. The use of different terms or reference numerals for similar features in different embodiments does not necessarily imply differences other than those which may be expressly set forth. Accordingly, the present invention is intended to be described solely by reference to the appended claims, and not limited to the preferred embodiments disclosed herein.

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

GENERAL

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

The various headings and titles used herein are for the convenience of the reader, and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. An orthopedic fixation frame assembly, comprising
a first fixation plate comprising a plurality of separate first plate components, each of the plurality of separate first plate components having an upper surface, a lower surface and a side surface, a plurality of first openings formed in each of the plurality of separate first plate components extending from the upper surface to the lower surface, at least a portion of the plurality of first openings being positioned along a peripheral edge of each of the plurality of separate first plate components, and a plurality of second openings transverse to the plurality of first openings extending through each of the plurality of separate first plate components from the side surface, wherein at least a portion of the plurality of second openings are internally threaded, the plurality of separate first plate components assembled into a first closed loop shape to form the first fixation plate;
a second fixation plate spaced apart from the first fixation plate assembly, the second fixation plate comprising a plurality of separate second plate components assembled into a second closed loop shape to form the second fixation plate,
a compression plate attachable to at least one of the plurality of second openings;
a plurality of fixation rods connected to the first and second fixation plates, a first rod of the at least one of the rods positioned within at least one of the plurality of openings positioned along the peripheral edge of the first fixation plate, the first rod compressed between the compression plate and the first fixation plate, wherein a first thickness between the upper and lower surfaces of at least one of the plurality of separate first plate components at a location proximate to the portion of the plurality of first openings positioned along the peripheral edge of each of the plurality of separate first plate components is substantially greater than an average thickness between the upper and lower surfaces of the at least one of the plurality of separate first plate components.

2. The orthopedic fixation frame assembly of claim 1, wherein at least one of the plurality of fixation rods is externally threaded.

3. The orthopedic fixation frame assembly of claim 1, wherein the compression plate includes a depression proximate to a peripheral edge of compression plate.

4. The orthopedic fixation frame assembly of claim 3, further comprising a threaded portion within the depression proximate to the peripheral edge of the compression plate.

5. The orthopedic fixation frame assembly of claim 1, wherein first fixation plate comprises a raised plate section proximate to the plurality of openings positioned along the peripheral edge of the first fixation plate.

6. The orthopedic fixation frame assembly of claim 1, wherein at least one of the plurality of separate first plate components comprises a generally angular U-shape.

7. The orthopedic fixation frame assembly of claim 1, further comprising a variable angle rod connector positioned between the between the first and second fixation plates.

8. The orthopedic fixation frame assembly of claim 1, wherein the compression plate is secured to the first fixation plate by a plurality of threaded connectors.

9. An external fixation device for attachment to a lower extremity of a patient, the device comprising,
a first fixation plate having an upper surface, a lower surface and a peripheral edge surface, the first fixation plate comprising a plurality of first plate subcomponents secured into a closed loop shape, wherein a plurality of first openings in the fixation plate are positioned proximate to the peripheral edge surface, the plurality of first openings extending from the upper surface to the lower surface,
wherein a first thickness between the upper and lower surfaces of the first fixation plate at a location proximate to at least one of the plurality of first openings is substantially greater than an average thickness between the upper and lower surfaces of the first fixation plate, and
a plurality of second openings positioned transverse to the plurality of first openings extending through the first fixation plate, the plurality of second opening including internally threaded portions adapted to receive a plurality of threaded connectors which compress a compression plate against the peripheral edge surface, wherein at least one fixation rod is sandwiched between the peripheral edge and the compression plate to thereby releasably secure the at least one fixation rod to the first fixation plate at a desired location and orientation.

10. A method for externally fixating an extremity, the method comprising:
providing an external fixation frame having a first modular support plate assembled from a plurality of first plate subcomponents and a second modular support plate assembled from a plurality of second plate subcomponents, the first and second modular support plates positioned around the extremity, the first and second support plates spaced apart from each other;
connecting a first support rod using a first connecting device to the first modular support plate, the first support rod connected by a second connecting device to the second modular support plate,
connecting a second support rod using a third connecting device to the first modular support plate and connecting the second support rod using a fourth connecting device to the second modular support plate; and
the first and second support rods being spaced apart from each other and maintaining the first and second modular support plates in a substantially rigid and fixed relationship relative to each other;
wherein at least one of the plurality of first and second plate subcomponents can be selectively removed from the first and second modular support plates while maintaining a remainder of the plurality of first and second plate subcomponents in a substantially rigid and fixed relationship relative to each other.

11. The method of claim 10, wherein at least one of the plurality of first and second plate subcomponents of the first and second modular support plates are U-shaped plates with substantially straight legs.

12. The method of claim 10, wherein the first and second connecting devices are fully removable from the first and second modular support plates.

13. The method of claim 10, wherein the first and second connecting devices are secured to the first and second modular support plates by externally accessible bolts.

14. The method of claim 10, wherein the first and second connecting devices are secured to the first and second modular support plates by externally accessible bolts that mate with internally positioned nuts.

15. The method of claim 10, wherein a bone within the extremity is directly attached to at least two bone connection devices, the at least two bone connection devices each attached to the external fixation frame.

16. The method of claim 15, wherein a first bone connection device of the at least two bone connection devices is attached to the first modular support plate and a second bone connection device of the at least two bone connection devices is attached to the second modular support plate.

17. The method of claim 10, wherein the extremity comprises a lower extremity.

18. The method of claim 10, wherein the extremity comprises an upper extremity.

* * * * *